United States Patent [19]

Bingham, Jr.

[11] 4,240,988

[45] Dec. 23, 1980

[54] METHOD OF STABILIZATION OF KINETICALLY CONTROLLED TRIARYL PHOSPHITE-HALOGEN COMPOUNDS

[75] Inventor: Alpheus Bingham, Jr., Lafayette, Ind.

[73] Assignee: Eli Lilly and Company, Indianapolis, Ind.

[21] Appl. No.: 8,648

[22] Filed: Feb. 1, 1979

[51] Int. Cl.$^3$ ............................................. C07F 9/14
[52] U.S. Cl. ..................................... 260/989; 260/960
[58] Field of Search ................................ 260/989, 960

[56] References Cited

U.S. PATENT DOCUMENTS 2,114,866  4/1938  Vaughn ............................ 260/989 X

*Primary Examiner*—Anton H. Sutto
*Attorney, Agent, or Firm*—Steven R. Lammert; Arthur R. Whale

[57] ABSTRACT

The kinetically controlled products of the reaction of triaryl phosphites and bromine or chlorine are stabilized by the presence of tertiary amine bases or halide complexing reagents. The stabilized halogenating reagents are useful in the preparation of 3-halo-3-cephem antibiotic compounds.

22 Claims, No Drawings

METHOD OF STABILIZATION OF KINETICALLY CONTROLLED TRIARYL PHOSPHITE-HALOGEN COMPOUNDS

BACKGROUND AND SUMMARY OF THE INVENTION

Recently it was discovered that when selected triaryl phosphites are reacted with chlorine or bromine in an inert organic solvent, intermediate kinetically controlled products are formed, which convert spontaneously at varying rates to the corresponding thermodynamically stable isomers. These newly discovered kinetically controlled triaryl phosphite-halogen compounds have been found to be superior halogenating agents when compared to the corresponding prior art recognized thermodyamically stable products. However, full advantage of the halogenating potential of the kinetically controlled products can only be realized if they are used prior to their rearrangement to the thermodynamically more stable, less reactive, form. Experimentally this has been achieved by preparing the kinetically controlled products at low temperatures immediately before they are utilized in subsequent halogenation reactions. Typically the triaryl phosphite-halogen kinetic compound is prepared in the solvent selected for the desired halogenation reaction; the substrate to be halogenated is then simply added to the resulting solution of the kinetic compound.

The present invention is directed to a method of stabilizing novel halogenating agents. More particularly the present invention is directed to a method of stabilizing the kinetically controlled product of the reaction of chlorine or bromine with a triaryl phosphite of the formula

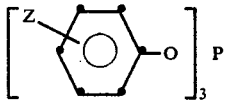

in solution in an inert organic solvent by adding a stabilizing amount of a tertiary amine base or a halide complexing agent.

Use of the present stabilizing techniques allows for the preparation and storage of otherwise unstable halogenating compounds which can be employed in the preparation of known 3-halo-3-cephem antibiotics.

DETAILED DESCRIPTION OF THE INVENTION

Triaryl phosphites of the formula

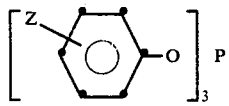

wherein Z is hydrogen, halo, $C_1-C_4$ alkyl or $C_1-C_4$ alkoxy, have been found to react with chlorine or bromine in a substantially anhydrous inert organic solvent to provide, initially, kinetically controlled products having the empirical formula

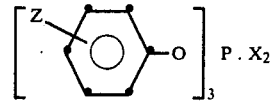

wherein Z is as defined above and X is Cl or Br.

The term "halo" in the definition of Z includes chloro, bromo or iodo. "$C_1-C_4$ Alkyl" includes methyl, ethyl, isopropyl, n-propyl, n-butyl, sec-butyl, tert-butyl and isobutyl. Representative "$C_1-C_4$ alkoxy" groups are methoxy, ethoxy, isopropoxy, tert-butoxy and n-butoxy.

The dot (.) in the general formula used to represent the kinetically controlled products is used simply to designate that molar equivalent amounts of halogen and triaryl phosphite are combined chemically and in a way that can be distinguished from that in the thermodynamically stable derivatives which have been known in the art and which typically have been drawn without the dot [e.g. $(PhO)_3PCl_2$]. The exact molecular form of the triaryl phosphite-halogen kinetic complexes described herein has not been established definitively; however, physical-chemical data do indicate that the kinetic product is one wherein the phosphorus center acquires some cationic character. Herein the terms "kinetic compound", "kinetic complex", "triaryl phosphite-halogen complex (compound)" kinetically controlled halogenating compound and "kinetically controlled product" are used synonomously.

Suitable triarylphosphites for the preparation of the kinetically controlled halogenating compounds include triphenyl phosphite, tri(p-methoxyphenyl)phosphite, tri(o-chlorophenyl)phosphite, tri(p-chlorophenyl)phosphite, tri(p-tolyl)phosphite, tri(o-tolyl)phosphite, tri(m-bromophenyl)phosphite, tri(p-iodophenyl)phosphite, tri-(p-n-propylphenyl)phosphite, tri(p-tert-butylphenyl)phosphite, tri(m-tolyl)phosphite, tri(p-isopropoxyphenyl)phosphite and the like. Triphenyl phosphite is preferred.

Any of a wide variety of inert organic solvents may be employed as the medium for the preparation of the kinetically controlled halogenating compounds. By "inert organic solvent" is meant an organic solvent which under the reaction conditions of the preparation do not enter into any appreciable reaction with either the reactants or the products. Since the halogenating compounds are susceptible to reaction with protic compounds, such compounds, including water, alcohols, amines (other than tertiary), thiols, organic acids and other such protic compounds should be excluded from the reaction medium.

A substantially anhydrous aprotic organic solvent is preferred. The term "substantially anhydrous" as used in the present description means that although anhydrous organic solvents are generally preferred, trace amounts of water, such as that often found in commercially available solvents, can be tolerated. Although the kinetic products described herein will react with any water present in the solvent medium, additional amounts of reagents can easily be added to compensate for the loss. It is preferred that conventional laboratory techniques be employed to dry the solvents employed and to exclude moisture from the reaction mixtures.

Suitable solvents include hydrocarbons, both aliphatic and aromatic, including pentane, hexane, heptane, octane, cyclohexane, cyclopentane, benzene toluene, o-, m- or p-xylene, mesitylene and the like; ethers, cyclic and acyclic such as diethyl ether, butyl ethyl ether, tetrahydrofuran, dioxane, 1,2-dimethoxyethane and the like; carboxylic acid esters such as ethyl acetate, methylformate, methyl acetate, amyl acetate, n-butyl acetate, sec-butyl acetate, methyl propionate, methyl butyrate and the like; nitriles such as acetonitrile, propionitrile, butyronitrile and the like; halogenated hydrocarbons, both aromatic and aliphatic, such as chloroform, methylene chloride, carbon tetrachloride, 1,2-dichloroethane (ethylene dichloride), 1,1,2-tri-chloroethane, 1,1-dibromo-2-chloroethane, 2-chloropropane, 1-chlorobutane, chlorobenzene, fluorobenzene, o-, m-, or p-chlorotoluene, o-, m-, or p-bromotoluene, dichlorobenzene and the like; and nitro compounds such as nitromethane, nitroethane, 1- or 2-nitropropane, nitrobenzene and the like.

The particular inert organic solvent employed as a medium for the preparation of the kinetically controlled triaryl phosphite-halogen compounds or as a medium for their use in halogenation processes is not critical; however, such solvents properties as polarity, melting or boiling point, and ease of isolation of halogenated products may be considered in selecting a most suitable solvent.

Preferred solvents for the preparation of the kinetically controlled products are hydrocarbons, especially aromatic hydrocarbons, and halogenated hydrocarbons.

If a halogenating compound derived from the kinetically controlled reaction of a triaryl phosphite and chlorine or bromine is allowed to stand in solution it converts or isomerizes to the corresponding thermodynamic compound at varying rates depending on, among other things, the nature of the triaryl phosphite, the halogen, the solvent and the solution temperature. Experimental data has also shown that the presence of an acid (HX) or an excess of triaryl phosphite will enhance the rate of conversion of the kinetic to the thermodynamic product.

Using $^{31}P$ nuclear magnetic resonance spectroscopy, the half-life of the kinetically controlled product from the reaction of triphenyl phosphite and chlorine in methylene chloride at room temperature was determined to be about 8 hours. A half-life of about 39 hours was observed for the triphenyl phosphite-bromine kinetic complex under the same conditions. As mentioned above the observed half-life (rate of conversion) for any given kinetic complex described herein can be affected by the solvent and by the presence of a hydrogen halide acid (HX) or excess triaryl phosphite. Thus for example, a shorter half life will be observed where the solvent for the preparation of kinetic complex has not been rigorously dried; the hydrogen halide acid produced from reaction of the kinetic complex with the moisture present in the solvent will enhance the rate of conversion to the stable form. Table I presents a summary of several properties of the kinetic product and the corresponding thermodynamic product of the reaction of triphenyl phosphite and chlorine.

TABLE I

| Kinetic product | Thermodynamic product |
|---|---|
| 1. $^{31}P$ nmr (CH$_2$Cl$_2$) − 3.7 ppm* | 1. $^{31}P$ nmr (CH$_2$Cl$_2$) + 22.7 ppm* |
| 2. $t_{1/2}$ = ≃ 8 hours at room temperature in methylene chloride | 2. Stable at room temperature |
| 3. ir (CH$_2$Cl$_2$) 1120–1190 (vs), 1070 (vs), 1035 (s), 1010 (vs), 990 (vs), 640 (m), 625 (m), 580 (w), 510 (s), 465 (w).** | 3. ir (CH$_2$Cl$_2$) 1130–1210 (vs), 1065 (vs), 1035 (s), 1010 (vs), 980 (vs), 625 (vw), 590 (m), 505 (s) 460 (s).** |
| 4. Hydrolyzes to give HCl and (PhO)$_3$PO | 4. Hydrolyzes to give inter alia HCl, PhOH (phenol) and (PhO)$_2$PCl |
| 5. Reacts with n-BuOH to give HCl, n-BuCl and PhO$_3$PO | 5. Reacts with n-BuOH to give HCl, PhOH (phenol), n-BuCl and (PhO)$_9$-(BuO)$_b$ POCl$_c$ wherein a,b,c, = 0, 1, 2 or 3 and a + b + c = 3 |

*Relative to $^{31}P$ of H$_3$PO$_4$; + indicates upfield shift; − indicates downfield shift
**vs = very strong, s = strong, m = medium, w = weak The term kinetically controlled product is a term of art which when used in reference to reactions yielding two (or more) products, refers to the product formed faster, regardless of its thermodynamic stability. If such a reaction is stopped well before the products achieve thermodynamic equilibrium, the reaction is said to be kinetically controlled since more of the faster formed product will be present. In some cases, including the reaction of triaryl phosphites and chlorine or bromine in inert organic solvents, the rate of formation of the kinetic product and the rate of thermodynamic equilibrium are such that the kinetically controlled product can be prepared and utilized before any significant amount of the kinetically controlled product isomerizes to the thermodynamically stable product. To maximize the production and stability of the kinetically controlled product, reaction conditions are selected so as to minimize the potential for thermodynamic equilibrium of the initial product of the reaction. Most simply conditions for kinetic control in this instance are achieved both by lowering the reaction temperature and the temperature of the kinetic product after it is formed, and by minimizing the time allowed for thermodynamic equilibrium, such as by utilizing the kinetic product in a subsequent reaction shortly after it has been prepared.

Typically the reactants, a triarylphosphite and chlorine or bromine, are combined in a substantially anhydrous inert organic solvent at a temperature below about 30° C. Although the kinetically controlled products are formed at higher temperatures, such conditions favor more the rapid isomerization to the thermodynamically stable products. Preferably the halogenating compounds are prepared at temperatures at or below about 30° C. Minimum reaction temperatures are, of course, determined by the freezing point of the solvent employed for the preparation. Most preferred reaction temperatures are in the range of about −70° to about 0° C.

It has been found that the triaryl phosphite itself reacts to some extent with its kinetic product with chlorine or bromine, effectively increasing the rate of conversion to the corresponding thermodynamic product. It is preferred, therefore, but not required, that an excess of halogen be maintained in the reaction mixture during the formation of the halogenating compounds. This can be achieved practically by adding the triaryl phsophite to a solution of an equivalent amount of the halogen or by adding the halogen and the triaryl phosphite simultaneously to a quantity of inert organic solvent at the desired temperature. The co-addition of reagents is conducted at such a rate that the color of the halogen persits in the reaction mixture until the last drop of triaryl phosphite discharges the color. Alternatively excess halogen can be discharged using known halogen scavengers such as acetylenes, or olefins including alkenes, dienes, cycloalkenes, or bicycloalkenes. A preferred scavenger is a $C_2$ to $C_6$ alkene, for example, ethylene, propylene, butylene, or amylene.

The present invention is directed to a method of stabilizing the aforedescribed kinetically controlled products of the formula

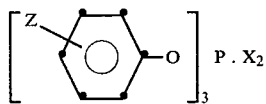

More particularly this invention is directed to a method of preventing or decreasing the rate of the conversion of the aforedescribed kinetically controlled products to the corresponding thermodynamically stable products, which have been found to be inferior as halogenating agents when compared to the kinetically controlled compounds.

Stabilization of the kinetically controlled products is effected by mixing those products in an inert organic solvent with a stabilizing amount of a tertiary amine base or a halide complexing agent.

Suitable tertiary amine bases are those having a $pK_b$ value of about 1 to about 10. Preferred tertiary amine bases are those having $pK_b$ values of about 6 to about 10. Exemplary of suitable tertiary amine bases for use in stabilizing the aforedescribed kinetically controlled compounds are trialkylamines such as trimethylamine, triethylamine, tri-n-propylamine, ethyldimethylamine, benzyldiethylamine and the like; dialkylarylamines such as dimethylaniline, diethylaniline, N,N-diethyl-4-methylaniline, N-methyl-N-ethylaniline, N,N-dimethyltoluidene and the like; cyclic and bicyclic tertiary amines such as pyridine, collidine, quinoline, isoquinoline, 2,6-lutidine, 2,4-lutidine, triethylene diamine, 1,5-diazobicyclo[4.3,0]nonene-5 (DBN), 1,5-diazobicyclo[5.4.0]undecene-5 (DBU), and the like; and polymeric tertiary amine bases, such as the copolymer formed from divinylbenzene and vinylpyridine described by Halensleben and Wurm in *Angew. Chem: Intl. Ed. Engl*, 15, 163 (1976). Pyridine is a most preferred tertiary amine base.

"Halide complexing agents" as used in the description of the present invention refers to compounds which are known to associate with halide ions under anhydrous conditions to provide more complex anions. A notable group of such compounds are known Lewis acid-metal halides, such as stannic chloride, antimony pentachloride or aluminum trichloride. Likewise phosphorus pentachloride is a suitable halogen complexing agent in that it associates with, for example, $Cl^-$ to form the $PCl_6^-$ anion. The kinetically controlled product, derived from a triaryl phosphite and bromine, in addition to being stabilized by the aforedescribed stabilizing agents, can be stabilized by adding excess bromine to its solution. Molecular bromine is a complexing agent in that it will react with $Br^-$ to form $Br_3^-$.

In general tertiary amine bases are preferred in the present method for stabilizing the kinetically controlled products detailed hereinabove. In fact, the tertiary amine base used to stabilize a triaryl phosphite-halogen kinetic compound can serve as a hydrogen halide scavenger in subsequent halogenation reactions utilizing the stabilized reagent.

A "stabilizing amount" as used in the description of the present invention is that amount of tertiary amine base or halide complexing agent which will prevent or decrease the rate of conversion of the described triaryl phosphite-halogen kinetic compounds to their corresponding thermodynamically stable derivatives. The amount of tertiary amine base or halide complexing agent used in the present method depends on the degree of stabilization desired. Even a relatively small amount, that is, less than 10 mole percent (0.1 mole of stabilizing agent per mole of kinetic compound) of a stabilizing agent, added to a solution of one of the aforedescribed kinetic products will result in a measurable increase in the half-life of the kinetic product. Typically about 10 to about 100 (1 equivalent) mole percent of the stabilizing agent is employed. Triphenyl phosphite-halogen kinetic products treated in solution with about equivalent amounts of tertiary amine base or halogen complexing agent show no conversion to the corresponding thermodynamically stable products even after prolonged periods of time. In general tertiary amine bases are more effective stabilizing agents when compared to the halide complexing agents in that fewer mole percent of tertiary amine base is needed to achieve any given degree of stabilization. For example, it has been determined that about 15–20 mole percent of pyridine is sufficient to stabilize triphenyl phosphite-chlorine kinetic complex for long term storage purpose.

In practice the method of the present invention can be carried out in several ways. For example, the kinetically controlled product can first be prepared in accordance with procedures detailed hereinbefore and subsequently stabilized by adding to its solution the desired amount of tertiary amine base or halide complexing agent. Alternatively the stabilizing tertiary amine or halide complexing agent can be mixed prior to formation of the kinetic product with either the triaryl phosphite, the halogen, or the inert organic solvent in which the kinetic product is to be prepared. The advantage of the later method is that the stabilizing agent is present in the reaction mixture as the kinetically controlled product is formed, allowing no opportunity for conversion to the corresponding thermodynamic product. A stabilized solution of the triaryl phosphite-halogen kinetic compound, containing little or none of the corresponding thermodynamic product is thereby obtained directly. Moreover, since the kinetically controlled products are stabilized as they are formed, their preparation can be conducted at higher temperatures without significant conversion to the thermodynamically stable products.

The kinetically controlled products of the reaction of a triaryl phosphite of the formula

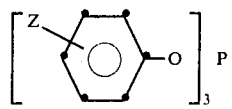

and chlorine or bromine in an inert organic solvent are most potent halogenating agents and can, under relatively mild conditions, halogenate many substrates cleanly and in high yield. The present invention allows the chemical practitioner to realize the full potential of these new halogenating compounds.

The halogenating compounds stabilized in accordance with the present inventions can be used in preparing known 3-halo-cephem antibiotics of the formula

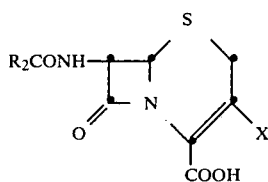

wherein X is chloro or bromo and $R_2CO$ is an acyl group derived from a carboxylic acid, from the corresponding 3-hydroxy cephem compounds. The reaction is conducted in an inert organic solvent and is typically carried out at a temperature below about 30° C., preferably at or below 0° C., using about a 10 percent mole excess of both the stabilized halogenating compound and a tertiary amine base, preferably pyridine, which may be present as the stabilizing agent of the halogenating agent. To prevent undesirable side reactions, the C-4 carboxylic acid function of the 3-hydroxy cephem starting materials is protected with one of the conventional carboxylic acid protecting groups. The course of the halogenation can be followed by thin-layer chromatography. The product 3-halocephem compounds can be isolated and purified using conventional laboratory techniques including chromatography, crystallization and recrystallization, filtration and trituration. Removal of the C-4 carboxylic acid protecting group and protecting groups, if any, on the C-7 acylamino group provides biologically active 3-halocephem compounds.

Alternatively, 7-acylamino-3-hydroxy-3-cephems react with about 2 equivalents of a halogenating compound stabilized in accordance with the present invention in an inert organic solvent in the presence of a tertiary amine base to provide the corresponding 3-halo-3-cephem imino halides of the formula

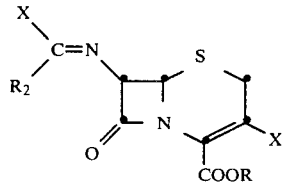

wherein X, R and $R_2$ are as defined above. The imino halides when treated with a 5–10 fold excess of an alcohol or diol provides 7-amino-3-halo-3-cephem compounds of the formula

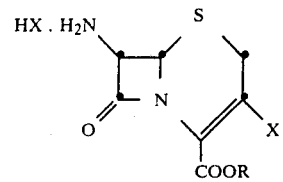

which can be acylated and subsequently deesterified by conventional procedures to provide known 3-halo-3-cephem compounds.

It should be noted too that the imino halides of other cephalosporins and penicillins can be prepared from the corresponding 7(or 6)-acylamino derivatives using the stabilized halogenating compounds in the presence of base.

The following examples are provided to further illustrate the present invention. It is not intended that this invention be limited in scope by reason of any of these examples.

EXAMPLE 1

Triphenyl phosphite-bromine kinetic complex (A) To a solution of 1.6 gm of bromine in 30 ml of methylene chloride at −45° C. was added a solution of 3.1 grams of triphenyl phosphite in 5 ml of methylene chloride. After warming the product solution to room temperature it was studied by $^{31}P$ nuclear magnetic resonance (nmr). The $^{31}P$ nmr spectrum initially indicated 1 major component having a signal at −3.7 ppm relative to the phosphoric acid $^{31}P$ resonance signal. This signal decreased in intensity with time as a signal at 22.4 ppm increased in intensity. From the $^{31}P$ nmr data the half-life (t ½) for the initial product was determined to be about 39 hours.

100 Mole percent excess of bromine (B) To a solution of 1.6 g. of bromine in 30 ml. of methylene chloride at −45° C. was added 1.55 g. of triphenyl phosphite in 5 ml. of methylene chloride. The $^{31}P$ nmr demonstrated that the resulting kinetic product was stabilized by the presence of a molar excess of bromine. No conversion to the corresponding thermodynamic product was noted after 9 hours.

The following table summarizes the results of several experiments relating to the stabilization of the triphenyl phosphite-bromine kinetic compound.

| Added Reagent | Approximate half-life (hours) |
| --- | --- |
| (A) Control | 39 |
| (B) Excess HCl | 20 |
| (C) 100 mole percent bromine | stable |
| (D) 200 mole percent pyridine | stable |

EXAMPLE 2

Triphenyl phosphite-chlorine kinetic complex (A) Chlorine and 20.0 gm. of triphenyl phosphite were added simultaneously to 100 ml. of methylene chloride at −15° to −20° C. maintaining a faint chlorine color throughout the co-addition. After warming the product solution to room temperature it was studied by $^{31}$P nmr. The $^{31}$P nmr spectrum of an aliquot the product solution initially indicated 1 component having a signal at −3.7 ppm relative to the phosphoric acid $^{31}$P nmr resonance signal. That signal decreased in intensity with time as a new signal at 22.7 ppm increased in intensity. From the $^{31}$P nmr data, the half-life for the initial product was determined to be about 8 hours.

The following table summarized the results of several experiments relating to the stabilization of the triphenyl phosphite-chlorine kinetic compound.

| Added Reagent | Approximate half-life (hours) |
| --- | --- |
| (A) Control | 8 |
| (B) 10 mole percent pyridine | 60 |
| (C) 50 mole percent pyridine | stable |
| (D) 100 mole percent pyridine | stable |
| (E) >100 mole percent pyridine | stable |
| (F) 50 mole percent pyridine plus excess HCl | 5 |
| (G) 100 mole percent PCl$_5$ | stable |
| (H) 100 mole percent AlCl$_3$ | stable |
| (I) 100 mole percent SnCl$_4$ | stable |

EXAMPLE 3

4'-Nitrobenzyl 7-amino-3-methyl-3-cephem-4-carboxylate hydrobromide

To a solution of 35.4 ml. of triphenyl phosphite-bromine complex prepared by reacting 6.67 ml. (25.4 mmol) of triphenyl phosphite and 1.30 ml. (25..4 mmol) of bromine in the presence of 2.10 ml. (26 mmol) of pyridine in 100 ml. of methylene chloride at −10° to −15° C. was added 4'-nitrobenzyl 7-phenoxyacetamido-3-methyl-3-cephem-4-carboxylate (9.67 g., 20 mmol). After 1 hour at −10° to −15° C., the reaction mixture was removed from the cooling bath. Isobutanol (13.88 ml., 150 mmol) was added. After stirring for 2 hours at room temperature the reaction mixture was filtered to provide 4.76 g. (55.3%) of the titled product. m.p. 179°–181° C. (decomp).

Anal. Calc. for C$_{15}$H$_{16}$N$_3$O$_5$SBr: C, 41.87; H, 3.75; N, 9.77; S, 7.45; Br, 18.57. Found: C, 42.04; H, 3.57; N, 9.54; N, 7.54; Br, 18.37.

nmr (DMSO d-6) δ2.2 (s, 3), 3.65 (bs, 2), 5.27 (m, 2, β-lactam-H), 5.42 (s, 2), and 7.6–8.4 (m, 4, ArH).

EXAMPLE 4

4'-Nitrobenzyl 7-amino-3-methyl-3-cephem-4-carboxylate hydrochloride using tri(p-chlorophenyl)phosphite-chlorine kinetic complex To 5.17 g. (12.5 mmol) of tri(p-chlorophenyl)phosphite and 0.27 ml. (3.28 mmol) of pyridine in 25 ml. of methylene chloride at −70° C. was added chlorine gas. Amylene (0.40 ml.) was added to discharge excess chlorine. To the resulting solution were added 4'-nitrobenzyl 7-phenoxyacetamido-3-methyl-3-cephem-4-carboxylate (2.42 g., 5 mmol) and pyridine (0.79 ml., 9.22 mmol) in 4 ml. of methylene chloride dropwise over 11 minutes. After 3 hours the cooling bath was removed and 6.94 ml. of isobutanol were added. After the reaction mixture had warmed to about −10° C., HCl gas was bubbled into the mixture for about 1 minute. After 15 minutes the reaction mixture was filtered to give 1.86 grams (96%) of the titled product as a white solid. m.p. 184°–185° C. (decomp).

EXAMPLE 5

4'-Nitrobenzyl 7-amino-3-chloro-3-cephem-4-carboxylate hydrochloride using tri(p-chlorophenyl)phosphite-chlorine kinetic complex To 10.34 g of tri(p-chlorophenyl)phosphite and 0.53 ml (6.5 mmol) of pyridine in 50 ml of methylene chloride at −70° was added chlorine in 15 ml of methylene chloride. Amyleme (0.52 ml) was added to discharge excess chlorine. To the resulting solution of the tri(p-chlorophenyl)phosphite-chlorine complex was added 4'-nitrobenzyl 7-phenoxyacetamido-3-hydroxy-3-cephem-4-carboxylate (5.28 g) using 10 ml of methylene chloride to wash the substrate into the reaction mixture. Then 1.57 ml (19.5 mmol) of pyridine in 9 ml of methylene chloride were added dropwise over 33 minutes. After 2 hours the reaction mixture was allowed to warm to 2°. Isobutanol (6.94 ml) was added, and HCl gas was bubbled through the mixture for 2 minutes. The mixture was evaporated in vacuo to a syrup to which was added 50 ml of ethyl acetate. The gun was triturated with about 100 ml of methanol. A white solid, tri(p-chlorophenyl)phosphate, was filtered. The filtrate was evaporated in vacuo to dryness. To the residue was added 15 ml of 1:1-toluene/ethyl acetate and just enough methanol to dissolve the gummy residue. Upon standing for about 5 minutes, 0.97 g of the titled product crystallized as a white solid. m.p. 184°–186° C. (decomp).

EXAMPLE 6

Benzyl 7-(1-chloro-2-phenylethylidene)-7-methoxy-3-acetoxymethyl-3-cephem-4-carboxylate To a solution of the triphenyl phosphite dichloride complex prepared from chlorine and 12.3 mmol of triphenyl phosphite in the presence of 0.1 ml of pyridine in 45 ml of methylene chloride at −15° C., were added 5.11 g (10 mmol) of benzyl 7-phenylacetamido-7-methoxy-3-acetoxymethyl-3-cephem-4-carboxylate and dropwise over 10 minutes a solution of 1.01 ml (12.5 mmol) of pyridine in 4 ml of methylene chloride. After 50 minutes at −15° to 10° C., 2.1 ml (30 mmol) of propylene oxide. After an additional 10 minutes (reaction temperature to 0° C.), the reaction mixture was washed with 25 ml of ice water, dried over CaCl$_2$ and evaporated in vacuo to 11 g of syrup. The product was triturated 3 times under carbon tetrachloride and then taken up in 50 ml of ether. The etheral solution was decanted from 0.5 g of precipitate and then evaporated in vacuo to about 25 ml. An oily product was obtained with the resulting etheral solution was diluted with 25 ml of hexane. The oil was washed twice with 1:1/hexane:ether and then evaporated in vacuo to a foam twice from carbon tetrachloride solutions to provide 2.5 g of the titled product: ir (CHCl$_3$) 1780 and 1730 cm$^{-1}$.

nmr (CDCl$_3$, pyridine d-5), δ1.96 (s, 3), 3.3 (Abq), 3.43 (s, 2), 3.93 (s, 2), 4.86 (ABq), 4.93 (s, 1), 5.25 (s, 1) and 7.3 (ArH).

I claim:

1. A method of preventing, or decreasing the rate of, the conversion of halogenating compounds of the general formula

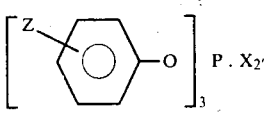

which compounds are the kinetically controlled products of the reaction of equivalent amounts of chlorine or bromine and a triaryl phosphite of the formula

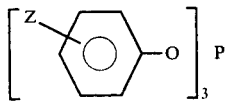

in a substantially anhydrous inert organic solvent, to the corresponding thermodynamically stable compounds, which method comprises mixing said halogenating compounds in an inert organic solvent with a stabilizing amount of a tertiary amine base, wherein in the above formulas X is Cl or Br, and Z is hydrogen, halo, $C_1$–$C_4$ alkyl or $C_1$–$C_4$ alkoxy.

2. The method of claim 1 wherein the tertiary amine base has a p$K_b$ value of about 6 to about 10.

3. The method of claim 2 wherein X is Br.

4. The method of claim 3 wherein Z is hydrogen.

5. The method of claim 2 wherein X is Cl.

6. The method of claim 5 wherein Z is hydrogen.

7. The method of claim 6 wherein about 10 to about 100 mole percent of tertiary amine base is employed.

8. The method of claim 7 wherein the tertiary amine base is pyridine.

9. The method of claim 8 wherein the inert organic solvent is an aromatic hydrocarbon or halogenated hydrocarbon.

10. A method of stabilizing halogenating compounds of the general formula

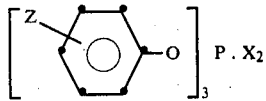

wherein X is Cl or Br and Z is hydrogen, halo, $C_1$–$C_4$ alkyl or $C_1$–$C_4$ alkoxy, which compounds are the kinetically controlled products of the reaction of equivalent amounts of a triaryl phosphite of the formula

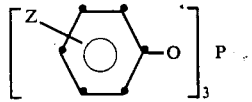

and chlorine or bromine in a substantially anhydrous inert organic solvent, which comprises mixing said halogenating compounds in an inert organic solvent with a stabilizing amount of a halide complexing agent selected from the group consisting of phosphorous pentachloride, aluminum trichloride, antimony pentachoride, stannic chloride and bromine; with the limitation that when X is Cl the halide complexing agent is not bromine.

11. The method of claim 10 wherein X is Br.

12. The method of claim 11 wherein Z is hydrogen.

13. The method of claim 12 wherein the halide complexing agent is bromine.

14. The method of claim 10 wherein X is Cl.

15. The method of claim 14 wherein Z is hydrogen.

16. The method of claim 15 wherein the inert organic solvent is an aromatic hydrocarbon or a halogenated hydrocarbon.

17. A method of preventing, or decreasing the rate of, the conversion of a compound having the empirical formula

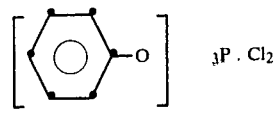

which
(a) has a $^{31}P$ nuclear magnetic resonance signal in methylene chloride at $-3.7$ ppm relative to that of phosphoric acid;
(b) has in methylene chloride an infrared spectrum which has the following characteristic absorptions; 1120–1190 (very strong), 1070 (very strong), 1035 (strong), 1110 (very strong), 990 (very strong), 640 (medium), 625 (medium), 580 (weak), 510 (strong) and 465 (weak);
(c) reacts with water to give HCl and triphenyl phosphate; and
(d) reacts with n-butanol to give HCl, n-butyl chloride, and triphenyl phosphate;

to the corresponding thermodynamically stable compound which comprises mixing said compound in an inert organic solvent with a stabilizing amount of a tertiary amine base or a halide complexing agent selected from the group consisting of phosphorus pentachloride, aluminum trichloride, antimony pentachloride, and stannic chloride.

18. The method of claim 17 wherein a tertiary amine base is employed.

19. The method of claim 18 wherein the tertiary amine base has a p$K_b$ value of about 6 to about 10.

20. The method of claim 19 wherein about 10 to about 100 mole percent of tertiary amine base is employed.

21. The method of claim 20 wherein the tertiary amine base is pyridine.

22. The method of claim 21 wherein the inert organic solvent is an aromatic hydrocarbon or a halogenated hydrocarbon.

* * * * *